(12) United States Patent
Imada et al.

(10) Patent No.: US 8,816,033 B2
(45) Date of Patent: Aug. 26, 2014

(54) RADICALLY CURABLE COMPOUND, CURED PRODUCT THEREOF, AND METHOD FOR PRODUCING THE COMPOUND

(75) Inventors: Tomoyuki Imada, Ichihara (JP); Takakazu Kage, Ichihara (JP); Norifumi Imaizumi, Ichihara (JP)

(73) Assignee: DIC Corporation, Tokyo (JP)

( * ) Notice: Subject to any disclaimer, the term of this patent is extended or adjusted under 35 U.S.C. 154(b) by 0 days.

(21) Appl. No.: 14/003,317

(22) PCT Filed: Mar. 5, 2012

(86) PCT No.: PCT/JP2012/055523
§ 371 (c)(1),
(2), (4) Date: Sep. 5, 2013

(87) PCT Pub. No.: WO2012/121195
PCT Pub. Date: Sep. 13, 2012

(65) Prior Publication Data
US 2013/0338329 A1  Dec. 19, 2013

(30) Foreign Application Priority Data
Mar. 8, 2011 (JP) .................. 2011-050128

(51) Int. Cl.
*C08F 20/10* (2006.01)
(52) U.S. Cl.
USPC ...................................... 526/323.1
(58) Field of Classification Search
USPC ............... 560/76, 80, 84, 95, 96, 100
See application file for complete search history.

(56) References Cited

FOREIGN PATENT DOCUMENTS

| JP | 09-157340 A | | 6/1997 |
|---|---|---|---|
| JP | WO2006 132139 | * | 12/2006 |
| JP | 201293784 | * | 1/2012 |
| WO | WO-2006/132139 A1 | | 12/2006 |

OTHER PUBLICATIONS

The English translation of a JP-2012 093784 was conducted on a website titled AIPN Japan Patent Office on Nov. 19, 2013.*
International Search Report dated Jun. 5, 2012, issued for PCT/JP2012/055523.

* cited by examiner

*Primary Examiner* — Brandon Fetterolf
*Assistant Examiner* — Blaine G Doletski
(74) *Attorney, Agent, or Firm* — Edwards Wildman Palmer LLP; James E. Armstrong, IV

(57) ABSTRACT

An object of the present invention is to provide a radically curable compound which produces cured products with excellent heat resistance, and in order to achieve the object, the present invention provides a radically curable compound represented by general formula (1) below. (In the formula, $R^1$ and $R^2$ are each independently an alkyl group having 1 to 8 carbon atoms, $R^3$ and $R^4$ are each independently a hydrogen atom or a methyl group, m and n are each independently an integer of 1 to 4, and X is an aromatic hydrocarbon group or an aromatic hydrocarbon group substituted by an alkyl group having 1 to 8 carbon atoms.)

(1)

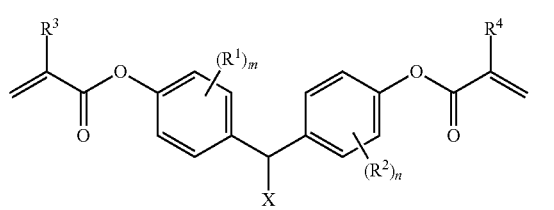

10 Claims, 2 Drawing Sheets

RADICALLY CURABLE COMPOUND, CURED PRODUCT THEREOF, AND METHOD FOR PRODUCING THE COMPOUND

TECHNICAL FIELD

The present invention relates to a radically curable compound which produces cured products with excellent heat resistance.

BACKGROUND ART

In recent years, techniques for electronic apparatuses have been significantly developed, and densities and performance of integrated circuits have been rapidly increased. Accordingly, printed circuit boards have been increased in density and wiring and advanced in component surface mounting and thus required to have higher precision and performance. In order to conform to higher densities and higher performance of integrated circuits, increases in performance of solder resists used as main materials of integrated circuits have been studied. However, build-up substrates having fine internal wiring have the problem of causing cracks referred to as a "popcorn phenomenon" at an interface between a solder resist and a sealing resin, and thus solder resists having higher heat resistance have been required.

Also, with increases in integration of integrated circuits, a nano-imprint method attracts attention as an ultrafine patterning method with a line width of 20 nm or less. The nano-imprint method is roughly divided into a thermal nano-imprint method and an optical nano-imprint method. The thermal nano-imprint method includes pressing a mold to a polymeric resin softened by heating to a glass transition temperature or more and then releasing the mold after cooling to transfer a microstructure to the resin on a substrate, and is thus capable of forming nano-patterns at relatively low cost and is expected to be applied to various fields. However, the thermal nano-imprint method requires the polymeric resin to be softened by heating and thus hardly uses a polymeric resin having a high glass transition temperature. Therefore, the nano-imprint method is difficult to apply to the electric/electronic field in which higher heat resistance has recently been required.

On the other hand, the optical nano-imprint method including photocuring a composition by light irradiation has no need to heat a mold material used for pattern transfer by pressing and is thus capable of imprinting at room temperature. Photocurable resins applied to optical nano-imprint include a radical polymerization type, an ion polymerization type, and a hybrid type thereof, and any one of the types of curable compositions can be used for nano-imprint applications. However, in general, radical polymerization-type photocurable compositions are widely studied because of a wide range of material selection.

When a nano-imprint material is used as a permanent film for fine processing of thin-film transistors of a liquid crystal display, a protective film of a liquid crystal color filter, a spacer, and other members of liquid crystal display devices, a cured product of the nano-imprint material is required to have high mechanical properties, transparency, light resistance, heat resistance, and the like, and particularly required to have high heat resistance. For example, epoxy(meth)acrylate resins having a biphenyl skeleton are known as materials which can produce cured products with high heat resistance (refer to, for example, Patent Literature 1), but do not have high heat resistance required in recent years.

CITATION LIST

Patent Literature

PTL 1: Japanese Unexamined Patent Application Publication No. 9-157340

SUMMARY OF INVENTION

Technical Problem

A problem to be solved by the present invention is to provide a radically curable compound which produces cured products with excellent heat resistance, and further provide a method for producing the compound.

Solution to Problem

As a result of intensive research, the inventors found that a cured product produced by curing a compound having a structure, which is obtained by, for example, producing a polycondensate of alkyl-substituted phenol and aromatic aldehyde and then reacting the polycondensate with a (meth)acrylic acid halide, has very high heat resistance, and the compound can be easily produced by this method, leading to the achievement of the present invention.

The present invention provides a radically curable compound represented by general formula (1) below,

[Chem. 1]

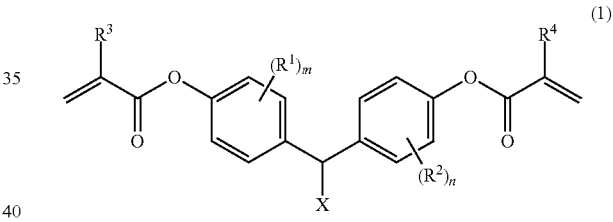

(in the formula, $R^1$ and $R^2$ are each independently an alkyl group having 1 to 8 carbon atoms, $R^3$ and $R^4$ are each independently a hydrogen atom or a methyl group, m and n are each independently an integer of 1 to 4, and X is an aromatic hydrocarbon group or an aromatic hydrocarbon group substituted by an alkyl group having 1 to 8 carbon atoms).

Also, the present invention provides a cured product produced by curing the radically curable compound with active energy rays or heat.

Further, the present invention provides a method for producing a radically curable compound, the method including reacting a polycondensate (A) of alkyl-substituted phenol (a1) and aromatic aldehyde (a2) with (meth)acrylic acid halide (B).

Advantageous Effects of Invention

A radically curable compound according to the present invention can produce a cured product having a very high level of heat resistance. Therefore, the radically curable compound of the present invention can be used as a material for solder resist and a material for nano-imprint which are required to have high heat resistance. Also, the radically curable compound of the present invention is a material having photocurability and being capable of optical molding and thus can be used as a casting material for the thermal nano-imprint method. When an engineering plastic for an electric/electronic material having a glass transition temperature (Tg) of over 200° C., such as polyphenylene ether (PPE) or the like having high heat resistance, is used as a thermoplastic resin used for a resist in the thermal nano-imprint method, a softening treatment temperature of the plastic is 300° C. or more, but a cured product of the radically curable compound of the present invention has very high heat resistance and thus can be used as a casting material.

Also, the radically curable compound of the present invention has benzene rings at a high density and thus has a more rigid skeleton, and thus a cured product thereof has high heat resistance. Further, the rigid skeleton causes the cured product to have high mechanical properties (impact resistance), high water resistance, and particularly high hardness. Therefore, the radically curable compound of the present invention can be preferably used for hard coating materials for films, such as triacetyl cellulose (TAC) and the like, which are used for polarizing plates of liquid crystal displays of a television, a video camera, a computer, a cellular phone, and the like; hard coating materials for transparent protective films which protect surfaces of various displays such as a liquid crystal display, a plasma display, an organic EL display, and the like; hard coating materials for optical lenses, and the like. The radically curable compound of the present invention can be easily produced by the production method of the present invention.

DESCRIPTION OF EMBODIMENTS

Figure 1:
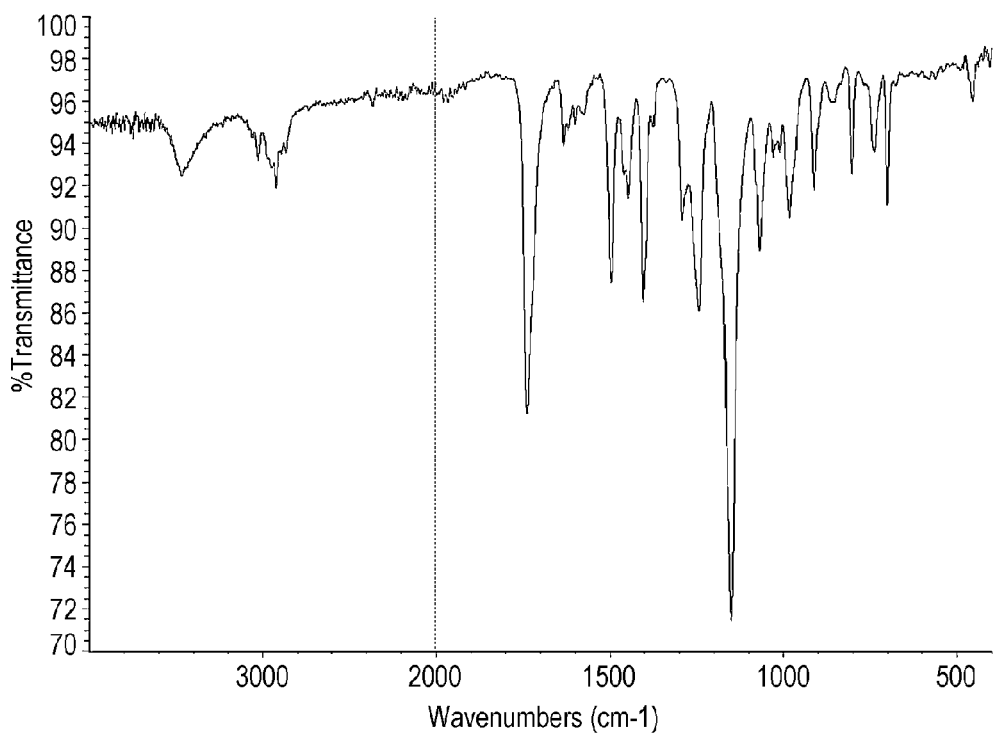
FIG. 1 is a chart of an IR spectrum of radically polymerizable compound (1) produced in Example 1.

A radically curable compound of the present invention provides is represented by general formula (1) below.

[Chem. 2]

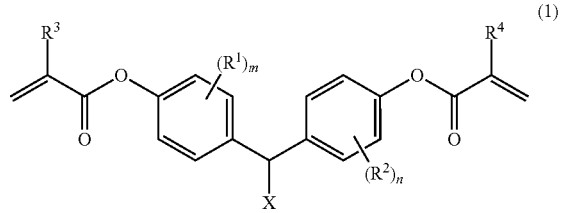

(In the formula, $R^1$ and $R^2$ are each independently an alkyl group having 1 to 8 carbon atoms, $R^3$ and $R^4$ are each independently a hydrogen atom or a methyl group, m and n are each independently an integer of 1 to 4, and X is an aromatic hydrocarbon group or an aromatic hydrocarbon group substituted by an alkyl group having 1 to 8 carbon atoms.)

In the general formula (1), $R^1$ and $R^2$ are each independently an alkyl group having 1 to 8 carbon atoms. The alkyl groups give high heat resistance to a cured product. Among the alkyl groups, a methyl group is preferred because it can impart high rigidity to a molecule by suppressing molecular motion, impart higher heat resistance to the cured product, impart an electron donating property to a phenolic benzene nucleus, and is industrially easily available.

In addition, $R^3$ and $R^4$ each independently represent a hydrogen atom or a methyl group. When $R^3$ and $R^4$ are each independently a hydrogen atom, a high curing rate and high adhesion to a substrate can be achieved, while when $R^3$ and $R^4$ are each independently a methyl group, low curing contraction, high water resistance, and high hardness can be achieved.

In the general formula (1), m and n are each independently preferably an integer of 1 to 3.

In view of the resultant cured product having excellent heat resistance, preferred examples of X in the general formula (1) include a benzene ring, a benzene ring substituted by an alkyl group having 1 to 8 carbon atoms, a naphthalene ring, and a naphthalene ring substituted by an alkyl group having 1 to 8 carbon atoms.

Examples of the radically curable compound having, as X in the general formula (1), a benzene ring or a benzene ring substituted by an alky group having 1 to 8 carbon atoms include the following compounds:

[Chem. 3]

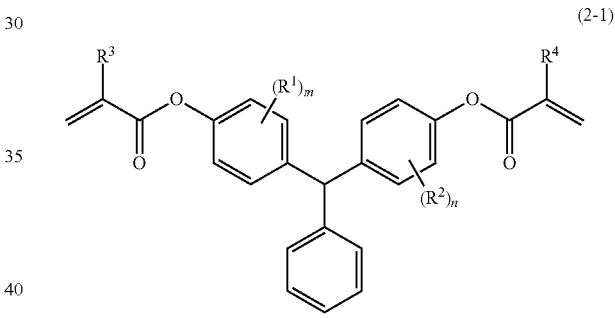

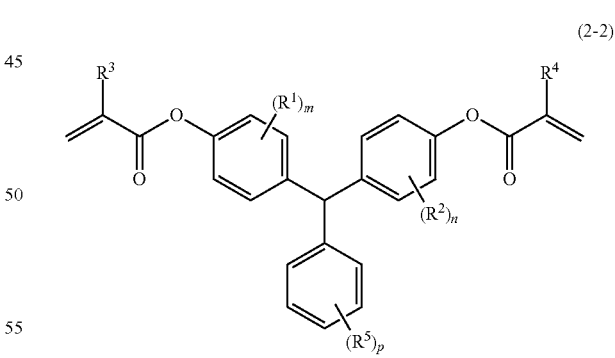

(In the formulae, $R^1$, $R^2$, and $R^5$ are each independently an alkyl group having 1 to 8 carbon atoms, $R^3$ and $R^4$ are each independently a hydrogen atom or a methyl group, m and n are each independently an integer of 1 to 4, and p is an integer of 1 to 5.)

Examples of the radically curable compound having, as X in the general formula (1), a naphthalene ring or a naphthalene substituted by an alky group having 1 to 8 carbon atoms include the following compounds:

[Chem. 4]

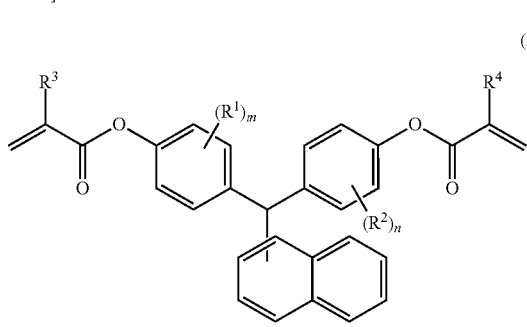

(3-1)

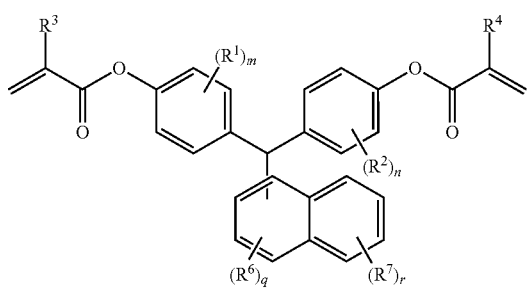

(3-2)

(In the formulae, $R^1$, $R^2$, $R^6$, and $R^7$ are each independently an alkyl group having 1 to 8 carbon atoms, $R^3$ and $R^4$ are each independently a hydrogen atom or a methyl group, m and n are each independently an integer of 1 to 4, and a total of q and r is an integer of 1 to 7.)

Examples of the radically polymerizable compound represented by the general formula (3-1) include compounds represented by general formula (3-1-1) and general formula (3-1-2) below. In addition, examples of the radically polymerizable compound represented by the general formula (3-2) include compounds represented by general formula (3-2-1) and general formula (3-2-2) below.

[Chem. 5]

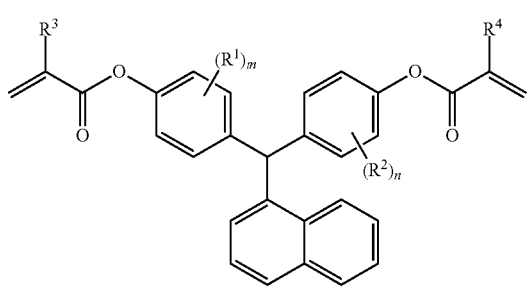

(3-1-1)

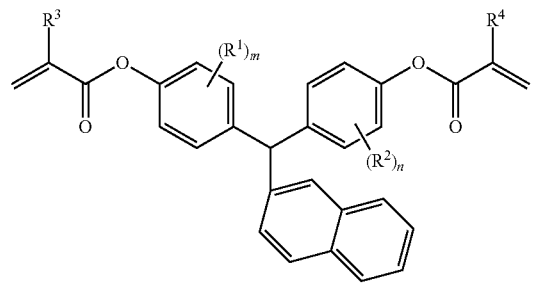

(3-1-2)

(In the formulae, $R^1$ and $R^2$ are each independently an alkyl group having 1 to 8 carbon atoms, $R^3$ and $R^4$ are each independently a hydrogen atom or a methyl group, and m and n are each independently an integer of 1 to 4.)

[Chem. 6]

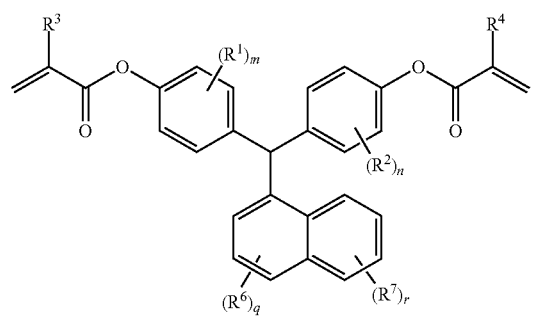

(3-2-1)

(3-2-2)

(In the formulae, $R^1$, $R^2$, $R^6$, and $R^7$ are each independently an alkyl group having 1 to 8 carbon atoms, $R^3$ and $R^4$ are each independently a hydrogen atom or a methyl group, m and n are each independently an integer of 1 to 4, and a total of q and r is an integer of 1 to 7.)

Among these radically curable compounds of the present invention, the radically curable compound having, as X in the general formula (1), a structure substituted by an alkyl group having 1 to 8 carbon atoms is preferred because it has good solvent solubility. Specifically, radically curable compounds represented by the general formula (2-2), the general formula (3-2), the general formula (3-2-1), and the general formula (3-2-2) are preferred.

The radically curable compound of the present invention can be easily produced by the production method of the present invention in which, for example, a polycondensate (A) of alkyl-substituted phenol (a1) and aromatic aldehyde (a2) is reacted with (meth)acrylic acid halide (B). In the present invention, "(meth)acrylic acid" refers to one or both of "acrylic acid" and "methacrylic acid".

The alkyl-substituted phenol (a1) is a compound having alkyl groups substituted for part or all of the hydrogen atoms bonded to a phenol aromatic ring. The alkyl groups are, for example, alkyl groups having 1 to 8 carbon atoms, and particularly methyl groups are preferred. Examples of the alkyl-substituted phenol (a1) include monoalkylphenols such as o-cresol, m-cresol, p-cresol, o-ethylphenol, m-ethylphenol, p-ethylphenol, p-octylphenol, p-tert-butylphenol, o-cyclohexylphenol, m-cyclohexylphenol, p-cyclohexylphenol, and the like; dialkylphenols such as 2,5-xylenol, 3,5-xylenol, 3,4-xylenol, 2,4-xylenol, 2,6-xylenol, and the like; trialkylphenols such as 2,3,5-trimethylphenol, 2,3,6-trimethylphenol, and the like. Among these alkyl-substituted phenols, those having two alkyl groups as substituents of a phenol aromatic ring are preferred, and 2,5-xylenol and 2,6-xylenol are particularly preferred. These alkyl-substituted phenols (a1) can be used alone or in combination of two or more.

The aromatic aldehyde (a2) is a compound having at least one aldehyde group in an aromatic ring. When an aromatic aldehyde having an aromatic ring substituted by an alkyl group having 1 to 8 carbon atoms is used as the aromatic aldehyde (a2), the radically curable compound having good solvent solubility, specifically the radically curable compounds represented by the general formula (2-2), the general formula (3-2), the general formula (3-2-1), and the general formula (3-2-2), can be produced.

Examples of the aromatic aldehyde (a2) include benzaldehyde; hydroxybenzaldehydes such as salicylaldehyde, m-hydroxybenzaldehyde, p-hydroxybenzaldehyde, and the like; dihydroxybenzaldehydes such as 2,4-dihydroxybenzaldehyde, 3,4-dihydroxybenzaldehyde, and the like; alkylbenzaldehydes such as p-tolualdehyde, cuminaldehyde, and the like; alkoxybenzaldehydes such as anisaldehyde, 3,4-dimethoxybenzaldehyde, and the like; vanillic compounds such as vanillin, ortho-vanillin, iso-vanillin, ethyl vanillin, and the like; phthalaldehydes such as terephthalaldehyde, isophthalaldehyde, and the like; naphthoaldehydes such as 1-naphthoaldehyde, 2-naphthoaldehyde, and the like: and hydroxynaphthoaldehydes such as 2-hydroxy-1-naphthoaldehyde, 6-hydroxy-2-naphthoaldehyde, and the like. Among these aromatic aldehydes, at least one aldehyde selected from the group consisting of benzaldehydes, hydroxybenzaldehydes, and naphthoaldehydes is preferred in view of industrially easy availability and excellent balance between heat resistance and alkali solubility. These aromatic aldehydes (a2) can be used alone or in combination of two or more.

Examples of a halide of the (meth)acrylic acid halide (B) include fluorine, chlorine, bromine, iodine, and astatine. Specific examples of the (meth)acrylic acid halide include (meth)acrylic acid chloride, (meth)acrylic acid bromide, (meth)acrylic acid iodide, and the like. Among these (meth)acrylic acid halides, (meth)acrylic acid chloride is preferred because of high reactivity and easy availability.

The method for producing the radically curable compound of the present invention is, for example, a method including three steps described below.

(Step 1)

A crude product containing the polycondensate (A) is produced in a reaction solution by polycondensation of the alkyl-substituted phenol (a1) and the aromatic aldehyde (a2) in the presence of an acid catalyst.

(Step 2)

The polycondensate (A) produced in the step 1 is isolated from the reaction solution.

(Step 3)

The polycondensate (A) isolated in the step 2 is reacted with the (meth)acrylic acid halide (B) in the presence of a base.

Examples of the acid catalyst used in the step 1 include acetic acid, oxalic acid, sulfuric acid, hydrochloric acid, phenolsulfonic acid, para-toluenesulfonic acid, zinc acetate, manganese acetate, and the like. These acid catalysts can be used alone or in combination of two or more. Among these acid catalyst, sulfuric acid and para-toluenesulfonic acid are preferred in view of excellent activity. The acid catalyst may be added before the reaction or during the reaction.

In the step 1, if required, the polycondensate may be produced in the presence of a solvent. Examples of the solvent include monoalcohols such as methanol, ethanol, propanol, and the like; polyols such as ethylene glycol, 1,2-propanediol, 1,3-propanediol, 1,4-butanediol, 1,5-pentanediol, 1,6-hexanediol, 1,7-heptanediol, 1,8-octanediol, 1,9-nonanediol, trimethylene glycol, diethylene glycol, polyethylene glycol, glycerin, and the like; glycol ethers such as 2-ethoxyethanol, ethylene glycol monomethyl ether, ethylene glycol monoethyl ether, ethylene glycol monopropyl ether, ethylene glycol monobutyl ether, ethylene glycol monopentyl ether, ethylene glycol dimethyl ether, ethylene glycol ethylmethyl ether, ethylene glycol monophenyl ether, and the like; cyclic ethers such as 1,3-dioxane, 1,4-dioxane, tetrahydrofuran, and the like; glycol esters such as ethylene glycol acetate and the like; and ketones such as acetone, methyl ethyl ketone, methyl isobutyl ketone, and the like. These solvents can be used alone or in combination of two or more. Among these solvents, 2-ethoxyethanol is preferred in view of excellent solubility of the resultant compound.

In the step 1, the reaction temperature of polycondensation of the alkyl-substituted phenol (a1) and the aromatic aldehyde (a2) is, for example, 60 to 140° C. Also, the reaction time is, for example, 0.5 to 100 hours.

In the step 1, a feed ratio [(a1)/(a2)] of the alkyl-substituted phenol (a1) to the aromatic aldehyde (a2) is preferably in a range of 1/0.2 to 1/0.5, more preferably in a range of 1/0.25 to 1/0.45, in terms of molar ratio because the unreacted alkyl-substituted phenol can be easily removed, and the reaction product with high purity can be produced in high yield.

An example of the polycondensate (A) resulting from the polycondensation in the step 1 is a compound represented by general formula (4) below.

[Chem. 7]

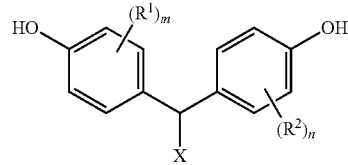

(4)

(In the formula, $R^1$ and $R^2$ are each independently an alkyl group having 1 to 8 carbon atoms, $R^3$ and $R^4$ are each independently a hydrogen atom or a methyl group, m and n are each independently an integer of 1 to 4, and X is an aromatic hydrocarbon group or an aromatic hydrocarbon group substituted by an alkyl group having 1 to 8 carbon atoms.)

Specific examples of the compound represented by the general formula (4) include compounds represented by general formula (4-1) and general formula (4-2) below.

[Chem. 8]

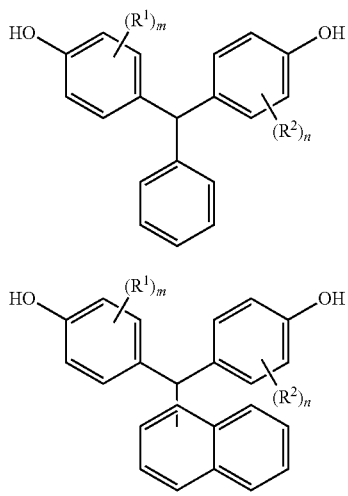

(4-1)

(4-2)

(In the formula, $R^1$ and $R^2$ are each independently an alkyl group having 1 to 8 carbon atoms, and m and n are each independently an integer of 1 to 4.)

Examples of the compound represented by the general formula (4-2) include compounds represented by general formulae below.

[Chem. 9]

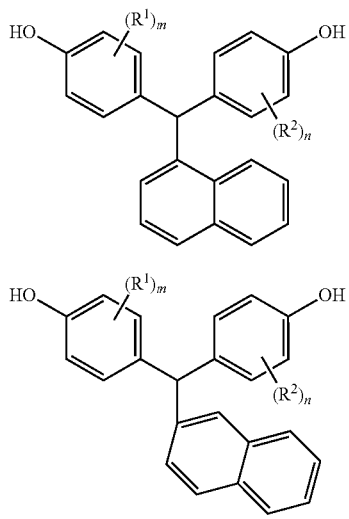

(4-2-1)

(4-2-2)

(In the formulae, $R^1$, $R^2$, m, and n are the same as the above.)

As described above, the radically curable compound having excellent solvent solubility can be produced by using, as the aromatic aldehyde (a2), an aromatic aldehyde having an aromatic ring substituted by an alkyl group having 1 to 8 carbon atoms. Examples of the polycondensate produced by using the aromatic aldehyde having an aromatic ring substituted by an alkyl group having 1 to 8 carbon atoms include compounds represented by general formulae below.

[Chem. 10]

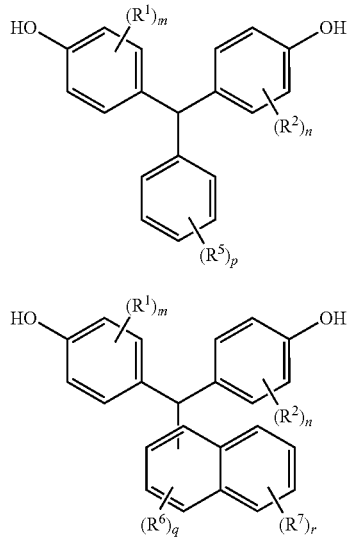

(5-1)

(5-2)

(In the formulae, $R^1$, $R^2$, and $R^5$ to $R^7$ are each independently an alkyl group having 1 to 8' carbon atoms, m and n are each independently an integer of 1 to 4, p is an integer of 1 to 5, and a total of q and r is an integer of 1 to 7.)

Examples of the compound represented by the general formula (5-2) include compounds represented by general formulae below.

[Chem. 11]

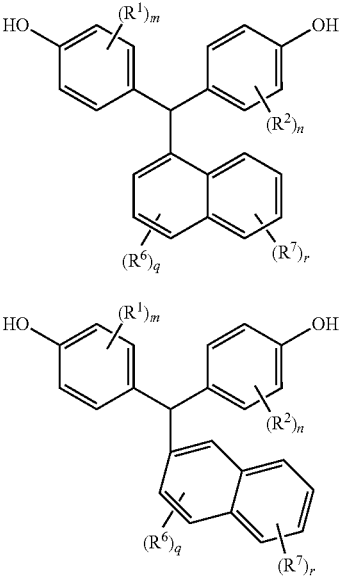

(5-2-1)

(5-2-2)

(In the formulae, $R^1$, $R^2$, $R^5$ to $R^7$, m, n, p are the same as the above.)

In the second step, the polycondensate (A) is isolated from the reaction solution. In this step, impurities such as unreacted compounds (a1) and (a2) are removed from the polycondensate (A) to increase crystallinity of the resultant radically curable compound of the present invention. As a result, the radically curable compound of the present invention can be easily closely packed. The radically curable compound of the present invention is cured as it is closely packed. Consequently, molecular motion of the cured product is suppressed, and heat resistance of 2 times or more as high as usual, i.e., a glass transition temperature of 400° C. or more, can be exhibited.

A method for isolating the polycondensate (A) from the reaction solution in the step 2 is, for example, a method in which the reaction solution is poured into a poor solvent (S1) which does not dissolve or slightly dissolves the reaction product to produce precipitates, which are then filtered off, the precipitates are dissolved in a solvent (S2) which dissolves the reaction product and is miscible with the poor solvent (S1) and again poured into the poor solvent (S1), and the resultant precipitates are filtered off. Examples of the poor solvent (S1) used in this step include water, monoalcohols such as methanol, ethanol, propanol, and the like; aliphatic hydrocarbons such as n-hexane, n-heptane, n-octane, cyclohexane, and the like; and aromatic hydrocarbons such as toluene, xylene, and the like. Among these poor solvents (S1), water and methanol are preferred because the acid catalyst can be simultaneously removed with high efficiency.

On the other hand, examples of the solvent (S2) include monoalcohols such as methanol, ethanol, propanol, and the like; polyols such as ethylene glycol, 1,2-propanediol, 1,3-propanediol, 1,4-butanediol, 1,5-pentanediol, 1,6-hexanediol, 1,7-heptanediol, 1,8-octanediol, 1,9-nonanediol, trimethylene glycol, diethylene glycol, polyethylene glycol, glycerin, and the like; glycol ethers such as 2-ethoxyethanol, ethylene glycol monomethyl ether, ethylene glycol monoethyl ether, ethylene glycol monopropyl ether, ethylene glycol monobutyl ether, ethylene glycol monopentyl ether, ethylene glycol dimethyl ether, ethylene glycol ethylmethyl ether, ethylene glycol monophenyl ether, and the like; cyclic ethers such as 1,3-dioxane, 1,4-dioxane, and the like; glycol esters such as ethylene glycol acetate and the like; and ketones such as acetone, methyl ethyl ketone, methyl isobutyl ketone, and the like. When water is used as the poor solvent (S1), acetone is preferred as the solvent (S2). Only one type or combination of two or more types of each of the poor solvent (S1) and the solvent (S2) can be used.

Examples of the base used in the step 3 include alkali metal hydroxides such as sodium hydroxide, potassium hydroxide, and the like; alkali metal carbonates such as sodium carbonate, potassium carbonate, cesium carbonate, and the like; tertiary amines such as triethylamine, trimethylamine, and the like; pyridine; and the like. Among the bases, potassium carbonate and tertiary amines are preferred in view of the ease of removal from the reaction system after the reaction between the polycondensate (A) and the (meth)acrylic acid halide (B), and potassium carbonate and triethylamine are more preferred.

If required, a solvent may be used in the step 3. Examples of the solvent include monoalcohols such as methanol, ethanol, propanol, and the like; polyols such as ethylene glycol, 1,2-propanediol, 1,3-propanediol, 1,4-butanediol, 1,5-pentanediol, 1,6-hexanediol, 1,7-heptanediol, 1,8-octanediol, 1,9-nonanediol, trimethylene glycol, diethylene glycol, polyethylene glycol, glycerin, and the like; glycol ethers such as 2-ethoxyethanol, ethylene glycol monomethyl ether, ethylene glycol monoethyl ether, ethylene glycol monopropyl ether, ethylene glycol monobutyl ether, ethylene glycol monopentyl ether, ethylene glycol dimethyl ether, ethylene glycol ethylmethyl ether, ethylene glycol monophenyl ether, and the like; cyclic ethers such as 1,3-dioxane, 1,4-dioxane, tetrahydrofuran, and the like; glycol esters such as ethylene glycol acetate and the like; and ketones such as acetone, methyl ethyl ketone, methyl isobutyl ketone, and the like. These solvents can be used alone or in combination of two or more. Among these solvents, tetrahydrofuran, methyl ethyl ketone, methyl isobutyl ketone are preferred in view of excellent solubility of the resultant compound.

In the step 3, the reaction temperature of reaction of the polycondensate (A) and the (meth)acrylic acid halide (B) is, for example, 20 to 80° C. Also, the reaction time is, for example, 1 to 30 hours.

In the step 3, a feed ratio of the polycondensate (A) to the (meth)acrylic acid halide (B) is preferably in a range of 1/1 to 1/3, more preferably in a range of 1/1 to 1/2.5, in terms of molar ratio [(A')/(B)] wherein A' represents the number of moles of phenolic hydroxyl groups possessed by the polycondensate (A) because the radically curable compound of the present invention can be produced with high purity in high yield.

The radically curable compound of the present invention, preferably the radically curable compound of the present invention which is produced through the above-described steps 1 to 3, can be cured by adding a polymerization initiator and applying active energy rays or heat to form a cured product.

When the radically curable compound of the present invention is cured by radical polymerization under irradiation with active energy rays, an intramolecular cleavage-type photopolymerization initiator or hydrogen abstraction-type photopolymerization initiator is used as the polymerization initiator.

Examples of the intramolecular cleavage-type photopolymerization initiator include acetophenone-based compounds such as 1-hydroxycyclohexyl phenyl ketone, diethoxy acetophenone, 2-hydroxy-2-methyl-1-phenylpropan-1-one, benzyl dimethyl ketal, 1-(4-isopropylphenyl)-2-hydroxy-2-methylpropan-1-one, 4-(2-hydroxyethoxy)phenyl-(2-hydroxy-2-propyl)ketone, 2-methyl-2-morpholino(4-thiomethylphenyl)propan-1-one, 2-benzyl-2-dimethylamino-1-(4-morpholinophenyl)-butanone, and the like; benzoins such as benzoin, benzoin methyl ether, benzoin isopropyl ether, and the like; acylphosphine oxide-based compounds such as 2,4,6-trimethylbenzoin diphenylphosphine oxide, bis(2,4,6-trimethylbenzoyl)-phenylphosphine oxide, and the like; azo compounds such as 1,1'-azobisisobutyronitrile, 1,1'-azobiscyclohexanecarbonitrile, 2-cyano-2-propylazoformamide, and the like; benzyl; methylphenyl glyoxyester; and the like.

Examples of the hydrogen abstraction-type photopolymerization initiator include benzophenone-based compounds such as benzophenone, o-benzoyl benzoic acid methyl-4-phenylbenzophenone, 4,4'-dichlorobenzophenone, hydroxybenzophenone, 4-benzoyl-4'-methyl-diphenyl sulfide, acrylated benzophenone, 3,3',4,4'-tetra(tert-butylperoxycarbonyl)benzophenone, 3,3'-dimethyl-4-methoxybenzophenone, and the like; thioxanthone-based compounds such as 2-isopropylthioxanthone, 2,4-dimethylthioxanthone, 2,4-diethylthioxanthone, 2,4-dichlorothioxanthone, and the like; aminobenzophenone-based compounds such as Michler's ketone, 4,4'-diethyl aminobenzophenone, and the like; 10-butyl-2-chloroacridone, 2-ethylanthraquinone; 9,10-phenanthrenequinone; camphor quinone; and the like.

Among the photopolymerization initiators, the acetophenone-based compounds such as 1-hydroxycyclohexyl phenyl ketone, 2-hydroxy-2-methyl-1-phenylpropan-1-one, 1-(4-isopropylphenyl)-2-hydroxy-2-methylpropan-1-one, 4-(2-hydroxyethoxy)phenyl-(2-hydroxy-2-propyl)ketone, 2-methyl-2-morpholino(4-thiomethylphenyl)propan-1-one, 2-benzyl-2-dimethylamino-1-(4-morpholinophenyl)-butanone, and the like, and benzophenone are preferred, and 1-hydroxycyclohexyl phenyl ketone is particularly preferred. These photopolymerization initiators can be used alone or in combination of two or more.

The amount of the photopolymerization initiator used is preferably 0.01 to 20 parts by mass, more preferably 0.1 to 15% by mass, and still more preferably 0.5 to 10 parts by mass relative to 100 parts by mass of the radically curable compound of the present invention. When electron beams described below are used as active energy rays, the photopolymerization initiator is not required.

Examples of the active energy rays used for curing the radically curable compound of the present invention include ultraviolet rays and ionizing irradiations such as electron beams, α-rays, β-rays, γ-rays, and the like. Examples of an energy source or curing apparatus which generates the active energy rays include a sterilization lamp, an ultraviolet lamp (black light), a carbon arc, a xenon lamp, a high-pressure mercury lamp for copying, a medium- or high-pressure mercury lamp, an ultrahigh-pressure mercury lamp, an electrodeless lamp, a metal halide lamp, an ArF excimer laser-, ultraviolet LED, ultraviolet light from a light source such as natural light or the like, electron beams from a scanning- or curtain-type electron beam accelerator, and the like.

When the radically curable compound of the present invention is cured by heat radical polymerization, a heat radical polymerization initiator is used. Examples of the heat radical polymerization initiator include organic peroxides such as benzoyl peroxide, di-tert-butyl peroxide, dicumyl peroxide, 3,3,5-trimethylhexanoyl peroxide, di-2-ethylhexyl peroxydicarbonate, methyl ethyl ketone peroxide, tert-butyl peroxyphthalate, tert-butyl peroxybenzoate, di-tert-butyl peroxyacetate, tert-butyl peroxyisobutylate, tert-butyl peroxy-2-hexanoate, tert-butyl peroxy-3,3,5-trimethylhexanoate, and the like; and azo compounds such as 1,1'-azobisisobutyronitrile, 1,1'-azobiscyclohexanecarbonitrile, 2-cyano-2-propylazoformamide, and the like. Among these heat radical polymerization initiators, benzoyl peroxide and 1,1'-azobisisobutyronitrile are preferred. In addition, these heat radical polymerization initiators can be used alone or in combination of two or more.

The amount of the heat radical polymerization initiator used is preferably 0.01 to 20 parts by mass, more preferably 0.1 to 15% by mass, and still more preferably 0.5 to 10 parts by mass relative to 100 parts by mass of the radically curable compound of the present invention.

EXAMPLES

The present invention is described in further detail below by giving examples. Methods for measuring an IR spectrum, a NMR spectrum, and a MS spectrum used for indentifying a compound are as described below.

[Method for Measuring IR Spectrum]
Measurement was performed by a KBr pellet method using "FT/IR-500" manufactured by JASCO Corporation.

[Method for Measuring $^1$H-NMR and $^{13}$C-NMR Spectra]
Structural analysis was performed by analyzing a DMSO-$d_6$ solution of a sample using "JNM-LA300" manufactured by JEOL Ltd.

[Method for Measuring TOF-MS Spectrum]
Measurement was performed by using "AXIMA-TOF$^2$" manufactured by Shimadzu Corporation.

Synthesis Example 1

Synthesis of Polycondensate (A-1)

In a 100 mL two-neck flask with a condenser and a thermometer, 3.66 g (30 mmol) of 2,5-xylenol and 1.06 g (10 mmol) of benzaldehyde were placed and dissolved in 10 mL of 2-ethoxyethanol. After 1 mL of sulfuric acid was added under cooling in an ice bath, the resultant solution was heated and stirred at 100° C. for 2 hours to induce reaction. After the reaction, the resultant solution was reprecipitated with water to produce a crude product containing a polycondensate of 2,5-xylenol and benzaldehyde. The crude product was redissolved in acetone and further reprecipitated with water, and then the resultant product was filtered off and dried under vacuum to produce 3.08 g of light brown crystals of polycondensate (A-1). As a result of identification of the polycondensate (A-1) by measurement of an IR spectrum, a NMR spectrum, and a MS spectrum, the polycondensate (A-1) was confirmed to be a compound represented by formula (3) below.

[Chem. 12]

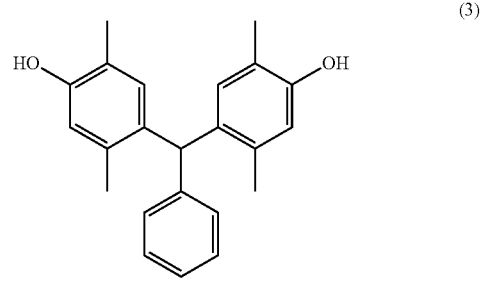

(3)

Example 1

Synthesis of Radically Curable Compound (1)

Figure 2:
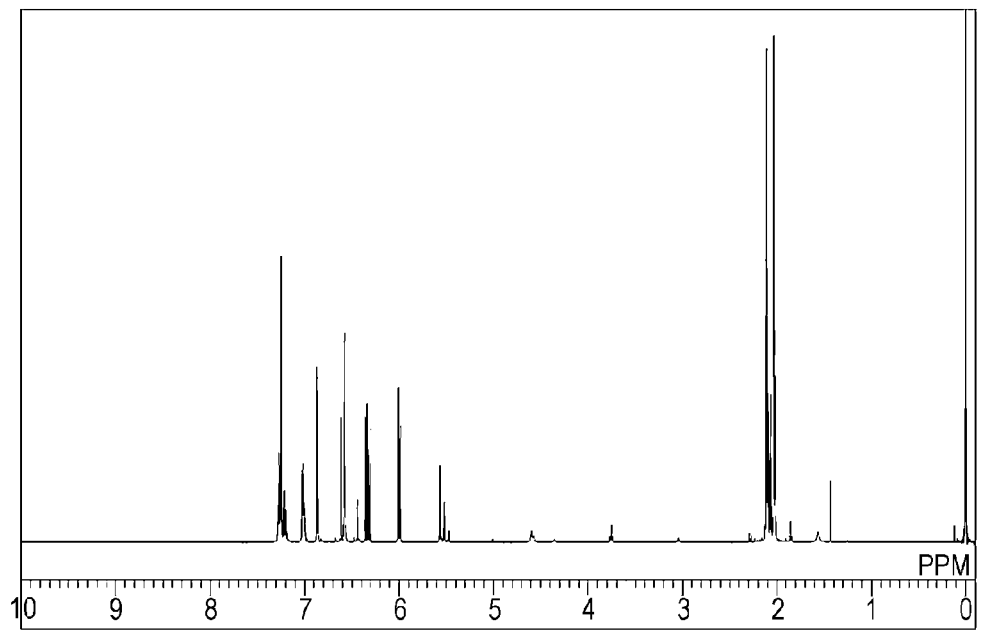
FIG. 2 is a chart of a $^1$H-NMR spectrum of radically polymerizable compound (1) produced in Example 1.
Figure 3:
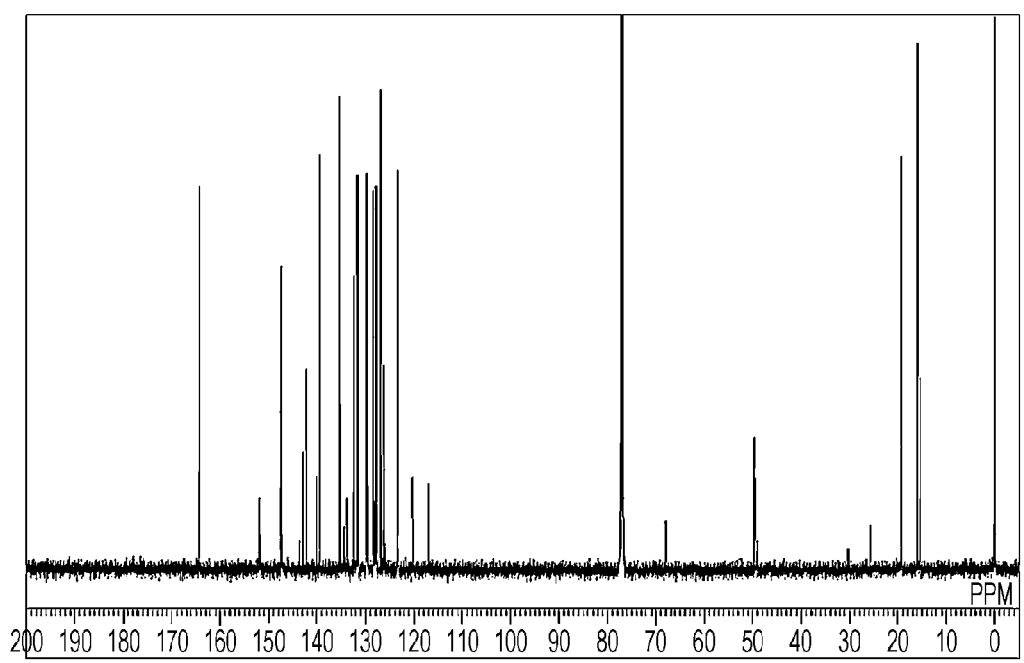
FIG. 3 is a chart of a $^{13}$C-NMR spectrum of radically polymerizable compound (1) produced in Example 1.

In a 100 mL two-neck flask with a condenser and a thermometer, 1.66 g (5 mmol) of the polycondensate (A-1) produced in Synthesis Example 1, 4.10 g (30 mmol) of potassium carbonate, and 10 mL of tetrahydrofuran were placed, and stirring was started. Then, 1.80 g (20 mmol) of acrylic acid chloride was added dropwise over 30 minutes under cooling in an ice bath, and then the resultant mixture was heated and stirred at 70° C. for 12 hours to induce reaction. After the reaction, the resultant solution was filtered to separate a solid content, and a filtrate was mixed with 30 ml of chloroform and washed 3 times with 50 ml of water. An organic layer as a lower layer was isolated and dried with sodium sulfate, and then the solvent was distilled off under reduced pressure to yield 1.38° g of white needle-like crystals of radically curable compound (1). As a result of identification of the radically curable compound (1) by measurement of an IR spectrum, a NMR spectrum, and a MS spectrum, the compound (1) was confirmed to be a compound represented by formula (4) below. FIG. 1 is a chart of the IR spectrum, FIG. 2 is a chart of the $^1$H-NMR spectrum, and FIG. 3 is a chart of the $^{13}$C-NMR spectrum.

[Chem. 13]

(4)

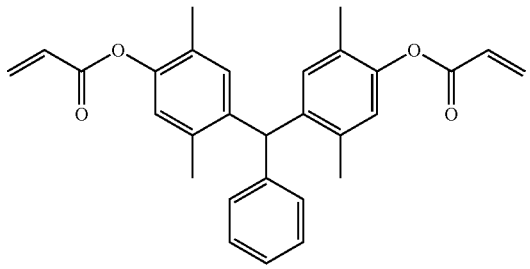

Peak values in each of the $^1$H-NMR spectrum, the $^{13}$C-NMR spectrum, and the TOF-MS spectrum are as described below.
[$^1$H-NMR Spectrum]
(ppm, 500 MHz, solvent: DMS-d$_6$, reference: TMS)
2.0-2.1 (12H; Ar—CH$_3$), 5.4-5.6 (1H; Ar—CH), 5.9-6.1 (4H; C—CH$_2$), 6.2-6.3 (2H; CO—CH—C), 6.5-7.3 (9H; Ar)
[$^{13}$C-NMR Spectrum]
(ppm, 125 MHz, solvent: DMSO-d$_6$, reference: TMS)
16.0, 19.2, 49.4, 123.4, 126.3, 126.9, 127.9, 128.3, 129.8, 131.7, 132.3, 135.4, 142.3, 143.0, 164.4
[TOF-MS Spectrum]
MNa$^+$=463.25

Comparative Synthesis Example 1

Synthesis of Bisphenol A (BPA)-Type Epoxy Acrylate

A reaction was performed at 95° C. between 188 parts by mass of bisphenol A (BPA)-type liquid epoxy resin ("EPICLON850" manufactured by DIC Corporation, epoxy equivalent 188 g/eq.) and 72% by mass of acrylic acid (ratio of number of epoxy groups:total number of carboxyl groups=1:1) to yield 253 parts by mass of BPA-type epoxy acrylate as a transparent viscous liquid.

Comparative Synthesis Example 2

Synthesis of Tetramethylbiphenyl-Type Epoxy Acrylate

A reaction was performed at 95° C. between 195 parts by mass of tetramethylbiphenyl-type liquid epoxy resin ("jER YX-4000H" manufactured by Mitsubishi Chemical Corporation, epoxy equivalent 195 g/eq.) and 72 parts by mass of acrylic acid (ratio of number of epoxy groups:total number of carboxyl groups=1:1) to yield 264 parts by mass of tetramethylbiphenyl-type epoxy acrylate as a transparent viscous liquid.

Comparative Synthesis Example 3

Synthesis of Cresol Novolac-Type Epoxy Acrylate

A reaction was performed at 100° C. between 214 parts by mass of o-cresol novolac-type epoxy resin ("EPICLON N-695" manufactured by DIC Corporation, epoxy equivalent 214 g/eq.) and 72 parts by mass of acrylic acid (ratio of number of epoxy groups:total number of carboxyl groups=1:1) to yield 273 parts by mass of cresol novolac-type epoxy acrylate as a yellow solid.

[Preparation of Cured Product]

Cured products were prepared as described in Examples 2 and 3 and Comparative Examples 1 to 6 using the acrylates produced in Example 1 and Comparative Synthesis Examples 1 to 3. According to methods described below, the glass transition temperature of each of the cured products was measured, and heat resistance of each cured product was evaluated. The results are shown in Table 1.

Example 2

In a Schlenk tube, 0.50 g of the radically curable compound (1) produced in Example 1, 0.05 g of a photopolymerization initiator ("Irgacure 184" manufactured by BASF Japan Ltd.; 1-hydroxycyclohexyl phenyl ketone), and 0.5 g of tetrahydrofuran were placed and freeze-dried in a nitrogen atmosphere. The reactor was sealed and irradiated with light for 3 hours using a high-pressure mercury lamp provided with a 340 nm band-pass filter to cause photocuring. The resultant content was reprecipitated with methanol, and the resultant precipitates were filtered off and dried under vacuum to yield 0.35 g of a cured product of the radically curable compound (1).

Example 3

In a Schlenk tube, 0.50 g of the radically curable compound (1) produced in Example 1, 0.01 g of a thermal polymerization initiator (azobisisobutyronitrile (manufactured by Wako Pure Chemical Co., Ltd.; abbreviated as "AIBN" hereinafter), and 0.5 g of dichloroethane were placed and freeze-dried in a nitrogen atmosphere. The reactor was sealed and heated at 70° C. for 12 hours to cause heat-curing. The resultant content was reprecipitated with methanol, and the resultant precipitates were filtered off and dried under vacuum to yield 0.21 g of a cured product of the radically curable compound (1).

Comparative Example 1

Except that the BPA-type epoxy acrylate produced in Comparative Synthesis Example 1 was used in place of the radically curable compound (1) used in Example 2, the same operation as in Example 2 was carried out to produce 0.23 g of a cured product of the BPA-type epoxy acrylate.

Comparative Example 2

Except that the BPA-type epoxy acrylate produced in Comparative Synthesis Example 1 was used in place of the radically curable compound (1) used in Example 3, the same operation as in Example 3 was carried out to produce 0.13 g of a cured product of the BPA-type epoxy acrylate.

Comparative Example 3

Except that the tetramethylbiphenyl-type epoxy acrylate produced in Comparative Synthesis Example 2 was used in place of the radically curable compound (1) used in Example 2, the same operation as in Example 2 was carried out to produce 0.35 g of a cured product of the tetramethylbiphenyl-type epoxy acrylate.

Comparative Example 4

Except that the tetramethylbiphenyl-type epoxy acrylate produced in Comparative Synthesis Example 2 was used in place of the radically curable compound (1) used in Example 3, the same operation as in Example 3 was carried out to produce 0.33 g of a cured product of the tetramethylbiphenyl-type epoxy acrylate.

Comparative Example 5

Except that the cresol novolac-type epoxy acrylate produced in Comparative Synthesis Example 3 was used in place of the radically curable compound (1) used in Example 2, the same operation as in Example 2 was carried out to produce 0.37 g of a cured product of the cresol novolac-type epoxy acrylate.

Comparative Example 6

Except that the cresol novolac-type epoxy acrylate produced in Comparative Synthesis Example 3 was used in place of the radically curable compound (1) used in Example 3, the same operation as in Example 3 was carried out to produce 0.42 g of a cured product of the cresol novolac-type epoxy acrylate.

[Method for Measuring Glass Transition Temperature of Cured Product]

A glass transition temperature (abbreviated as "Tg" hereinafter) was measured using a differential scanning calorimeter "differential scanning calorimeter (DSC) □100" manufactured by TA Instruments Inc.) in a nitrogen atmosphere under the conditions of a temperature range of 25 to 450° C. and a heating rate of 10° C./min.

[Evaluation of Heat Resistance of Cured Product]

The heat resistance was evaluated by the temperature Tg obtained by the measurement according to criteria below.
A: Tg of 300° C. or more
B: Tg of 250° C. or more and less than 300° C.
C: Tg of 200° C. or more and less than 250° C.
D: Tg of less than 200° C.

The raw materials before curing, Tg value, and the results of heat resistance evaluation of each of the cured products produced in Examples 2 and 3 and Comparative Examples 1 to 6 are summarized in Table 1. In Examples 2 and 3, Tg of ">400" represents that a glass transition point is not shown at a temperature higher than 400° C. and thermal decomposition takes place.

thus have heat resistance inferior to the cured products of the radically curable compound of the present invention.

The invention claimed is:
1. A compound of formula (2-1) or of formula (2-2) below,

[Chem. 1]

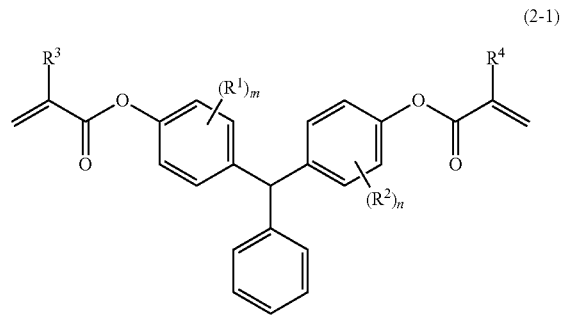

(2-1)

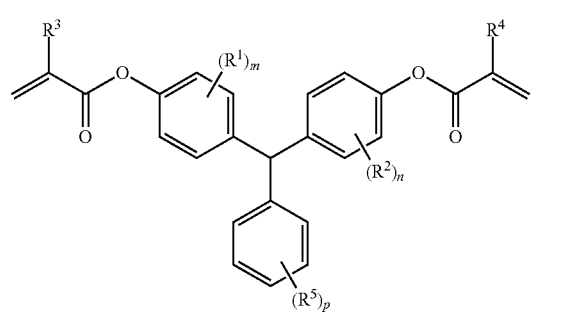

(2-2)

(in the formulae, $R^1$, $R^2$, and $R^5$ are each independently an alkyl group having 1 to 8 carbon atoms, $R^3$ and $R^4$ are each independently a hydrogen atom or a methyl group, m and n are each independently an integer of 1 to 4, and p is an integer of 1 to 5).

TABLE 1

| | | Example 2 | Example 3 | Comparative Example 1 | Comparative Example 2 | Comparative Example 3 | Comparative Example 4 | Comparative Example 5 | Comparative Example 6 |
|---|---|---|---|---|---|---|---|---|---|
| Component (%) | Photocurable compound (1) | 0.5 | 0.5 | | | | | | |
| | BPA-type epoxyacrylate | | | 0.5 | 0.5 | | | | |
| | Tetramethylbiphenyl-type epoxyacrylate | | | | | 0.5 | 0.5 | | |
| | Cresol novolac-type epoxyacrylate | | | | | | | 0.5 | 0.5 |
| | Irgacure 184 | 0.05 | | 0.05 | | 0.05 | | 0.05 | |
| | AIBN | | 0.01 | | 0.01 | | 0.01 | | 0.01 |
| Curing method | | Photo-curing | Heat curing | Photo-curing | Heat curing | Photo-curing | Heat curing | Photo-curing | Heat curing |
| Results of evaluation | Tg (° C.) | >400 | >400 | 158 | 163 | 171 | 178 | 221 | 229 |
| | Heat resistance | A | A | D | D | D | D | C | C |

The results shown in Table 1 reveal that the cured products (Examples 2 and 3) of the radically curable compound produced in Example 1 do not show a glass transition point at a temperature higher than 400 C and cause thermal decomposition, and thus have very good heat resistance.

On the other hand, the cured products of epoxy acrylates of Comparative Examples 1 to 6, which have been considered to have high heat resistance, have a Tg of 158° C. to 229° C. and 2. The compound according to claim 1, wherein the $R^1$ and $R^2$ are each independently a methyl group.
3. The compound according to claim 1, wherein the m and n are each independently an integer of 1 to 3.
4. A polymerized product produced by polymerizing the compound of claim 1 with active energy rays or heat.
5. A method for producing the compound of claim 1, the method comprising reacting a polycondensate (A) of alkyl-substituted phenol (a1) and aromatic aldehyde (a2) with (meth)acrylic acid halide (B), wherein the alkyl-substituted phenol (a1) is at least one selected from the group consisting of o-cresol, m-cresol, o-ethylphenol, m-ethylphenol, o-cyclohexylphenol, m-cyclohexylphenol, 2,5-xylenol, 3,5-xylenol, 2,6-xylenol, and 2,3,5-trimethylphenol, and the aromatic aldehyde (a2) is benzaldehyde.

6. The method for producing the compound according to claim 5, wherein the reacting a polycondensate (A) of alkyl-substituted phenol (a1) and aromatic aldehyde (a2) with (meth)acrylic acid halide (B), is conducted in three steps;
step 1: reacting the alkyl-substituted phenol (a1) and aromatic aldehyde (a2) in the presence of an acid catalyst, and
step 2: isolating a polycondensate (A) produced in step 1, and
step 3: reacting the isolated polycondensate (A) of step 2 with (meth)acrylic acid halide (B) in the presence of a base,
wherein the alkyl-substituted phenol (a1) is at least one selected from the group consisting of o-cresol, m-cresol, o-ethylphenol, m-ethylphenol, o-cyclohexylphenol, m-cyclohexylphenol, 2,5-xylenol, 3,5-xylenol, 2,6-xylenol, and 2,3,5-trimethylphenol, and the aromatic aldehyde (a2) is benzaldehyde.

7. The method for producing the compound according to claim 5, wherein the alkyl-substituted phenol (a1) is 2,5-xylenol or 2,6-xylenol.

8. A polymerized product produced by polymerizing the radically curable compound of claim 2 with active energy rays or heat.

9. A polymerized product produced by polymerizing the compound of claim 3 with active energy rays or heat.

10. The method for producing the compound according to claim 6, wherein the alkyl-substituted phenol (a1) is 2,5-xylenol or 2,6-xylenol.

* * * * *